(12) United States Patent
Imasaki et al.

(10) Patent No.: US 6,913,735 B2
(45) Date of Patent: Jul. 5, 2005

(54) METHANE/METHANOL PRODUCING SYSTEM

(75) Inventors: Kazuo Imasaki, Osaka (JP); Masahiro Mori, Tokyo (JP); Hiroyuki Nagayama, Tokyo (JP)

(73) Assignees: Institute for Laser Technology, Osaka (JP); Japan Aerospace Exploration Agency, Tokyo (JP); Mitsubishi Research Institute, Inc., Tokyo (JP)

( * ) Notice: Subject to any disclaimer, the term of this patent is extended or adjusted under 35 U.S.C. 154(b) by 410 days.

(21) Appl. No.: 10/175,874

(22) Filed: Jun. 21, 2002

(65) Prior Publication Data

US 2003/0006129 A1 Jan. 9, 2003

(30) Foreign Application Priority Data

Jun. 28, 2001 (JP) ........................................ 2001-196256

(51) Int. Cl.[7] .............................................. B01J 19/08
(52) U.S. Cl. ................... 422/186; 429/111; 244/158 R; 204/DIG. 3
(58) Field of Search ......................... 422/186; 429/111; 244/158 R; 204/DIG. 3

(56) References Cited

U.S. PATENT DOCUMENTS

| 3,808,428 A | * | 4/1974 | Barry et al. ................ 398/125 |
| 4,281,294 A | | 7/1981 | Volkin |
| 4,305,555 A | * | 12/1981 | Davis ...................... 244/158 R |
| 4,957,610 A | * | 9/1990 | Hawkins ..................... 205/340 |
| 5,269,288 A | * | 12/1993 | Stirbl et al. ................. 126/593 |

OTHER PUBLICATIONS

T. Weimer et al., "Methanol from Atmospheric Carbon Dioxide: A Liquid Zero Emission Fuel for the Future," Energy Conversion And Management, Elsevier Science Publishers, Oxford, GB, vol. 37, No. 6, Jun. 8, 1996, pp. 1351–1356, XP004039781.

* cited by examiner

*Primary Examiner*—Kishor Mayekar
(74) *Attorney, Agent, or Firm*—Wenderoth, Lind & Ponack, L.L.P.

(57) ABSTRACT

A methane or methanol producing system is proposed in which laser beams are generated in space by excitation of sunlight, transmitted onto land or sea without loss to obtain optical energy with high efficiency, and irradiated on a hydrogen producing device to produce industrially inexpensive hydrogen with high efficiency, thereby producing methane or methanol. A laser generating device for generating laser beams by exciting radiant light in laser rods by irradiation of sunlight is installed in space. The laser beams generated are transmitted to a light-receiving facility on land or on sea, and irradiated on a hydrogen generating device having a semiconductor electrode with a wavelength suitable for absorbing by the semiconductor electrode or by converting or shifting to a suitable wavelength. Using the hydrogen, methane or methanol is produced by a methane or methanol producing unit.

15 Claims, 14 Drawing Sheets

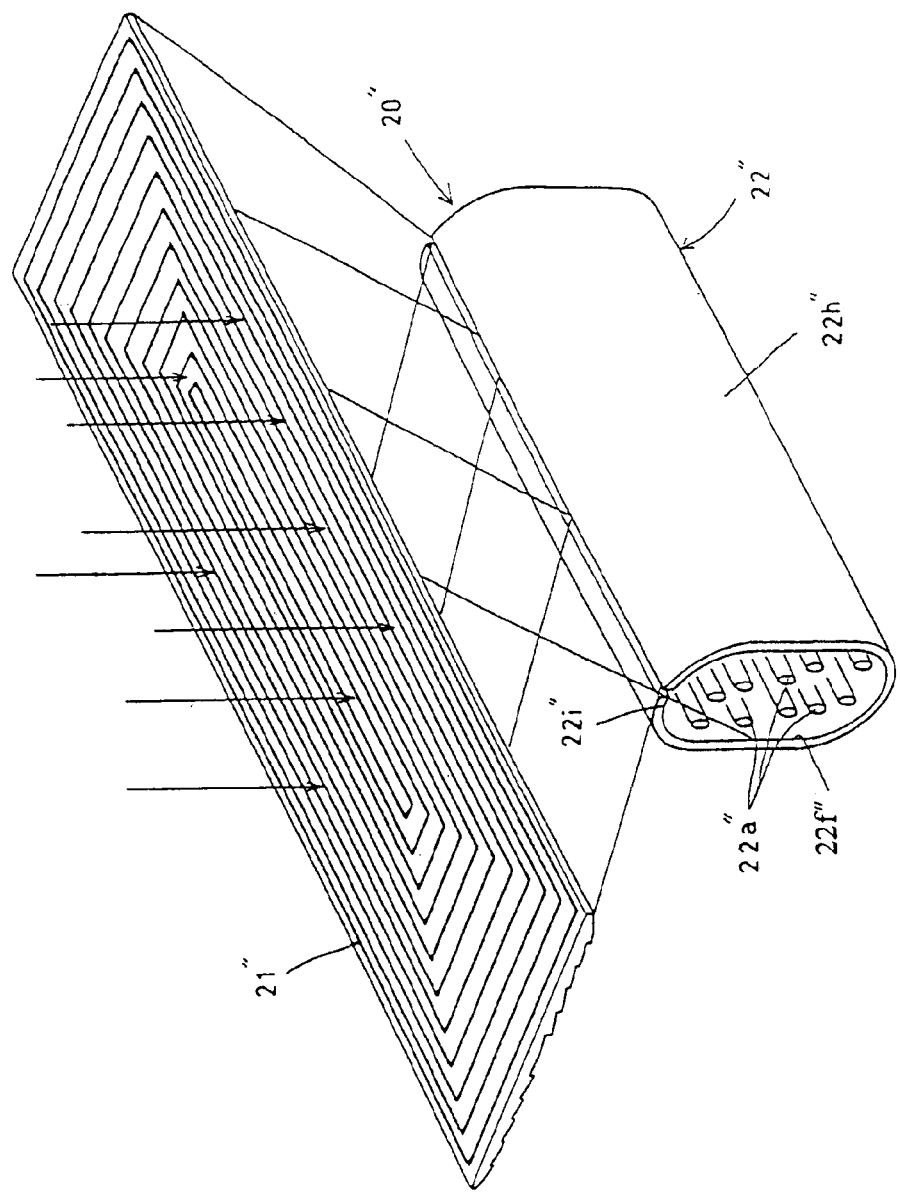

METHANE/METHANOL PRODUCING SYSTEM

BACKGROUND OF THE INVENTION

This invention relates to a system for irradiating laser beams excited by solar energy on water to decompose water and producing methane or ethanol from the hydrogen thus obtained.

As a method for industrially producing hydrogen, the most ordinary method is by electrolyzing water. But if fossil energy is used to generate electric power used for electrolysis, it creates a burden on the environment. In order to use hydrogen as completely clean energy, it is necessary to inexpensively and efficiently produce hydrogen from water in a large amount without using fossil fuel. From this viewpoint, the importance of producing hydrogen by electrolyzing water using the solar energy will increase in the future.

An example of the method for using hydrogen as energy is the use of methane and methanol. Methanol is a kind of alcohols obtained by synthesizing hydrogen with carbon monoxide (CO) or carbon dioxide ($CO_2$), and can be used to store hydrogen in a liquid state in a large amount. Methanol can be used as a fuel for fuel cells. If automotive engines are replaced with electric motors, there is a possibility that fuel cells may spread as the power source. By continuously supplying methanol together with an oxidizer such as air or oxygen, electric energy can be directly taken out. In view of such form of using hydrogen, there may arise a necessity for a system in which hydrogen obtained by electrolyzing water using the solar energy is converted to methanol and methanol is stored as fuel. Also, since methane is gaseous and can be more easily liquefied than hydrogen, it can be used as a substitute for natural gas.

An ordinary method of producing hydrogen using solar energy is to electrolyze water using electric energy obtained by solar battery generation. Another method is by optoelectrochemical reaction using semiconductor electrodes such as titanium oxide ($TiO_2$) (called titanium oxide (IV) or titanium dioxide to be precise). Hereinbelow called titanium oxide). It is known as the Honda/Fujishima effect.

In a method for producing hydrogen using such semiconductor electrodes, a semiconductor electrode of titanium oxide as an anode and a platinum (Pt) electrode as a cathode are oppositely arranged in two chambers filled with water and insulated from each other. When the sunlight is irradiated on the semiconductor electrode through a transmission window, a reaction occurs in which oxygen is produced, and hydrogen is produced at the platinum electrode, so that electric power is obtained through a load.

As semiconductor electrodes, various kinds are being studied besides $TiO_2$. As an example, JP patent publication 11-246985 proposes the use of zirconium dioxide ($ZrO_2$), tantalum oxide ($TaO_5$), niobium oxide ($NbO_5$), phosphorus indium (InP) and Pd alloys.

On the other hand, methanol ($CH_3OH$) is synthesized by reacting CO or $CO_2$ contained in e.g. generating exhaust gas with hydrogen industrially produced separately under high pressure.

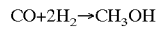

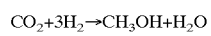

Methane can also be obtained under high pressure according to the following reaction formulas:

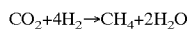

Further, it is also well-known that the methanol obtained in the above manner can be converted to gasoline at a high temperature of about 400° C. by use of synthesized zeolite ZSM-5 as a catalyst.

But with a method of producing hydrogen by the electric power of solar batteries, the energy efficiency is as low as about 20%. Also, on the ground where there are variations in diurnal difference, weather and season, only about 15% of the sunlight power at its peak can be utilized. Further, solar batteries themselves are expensive. In a method of producing hydrogen using a semiconductor electrode of e.g. titanium oxide, a usable wavelength range is theoretically determined by the material of the semiconductor electrode. Thus it is impossible to use the optical energy of the sunlight over its entire wavelength. Thus, in any of these methods, the energy conversion efficiency in decomposition of water by the sunlight is as low as about several percents. Therefore, they cannot be used as a method of industrially producing hydrogen. Thus it is also impossible to produce methane or methanol by use of hydrogen manufactured using the solar energy at a lower cost than it is now.

Also, methane and methanol can be produced from methane hydrate as one of ordinary methods. But, since carbon dioxide is generated during the combustion step, the content of carbon dioxide gas in the atmosphere increases. Thus, the same result comes as using fossil fuel. But if a method of converting the solar energy to laser beams in outer space is established, it is possible to markedly improve the energy conversion efficiency. It is expected that industrial use of hydrogen and methanol becomes possible. In this method, the content of carbon dioxide gas does not increase because carbon dioxide gas in the air is used in a cyclic manner.

An object of this invention is to provide a methane/methanol producing system in which hydrogen is produced at a low cost by utilizing the solar energy and methane or methanol is produced using the hydrogen produced.

SUMMARY OF THE INVENTION

According to this invention, there is provided a methane/methanol producing system comprising a laser generating device installed in space around the earth for generating laser beams by sunlight and transmitting the laser beams generated to a predetermined position on land or on the sea, a hydrogen generating unit comprising a semiconductor electrode for receiving the laser beams and generating hydrogen, the semiconductor electrode being irradiated with the laser beams to generate hydrogen by decomposition of water, and a methanol producing unit for producing methane or methanol by synthesizing the hydrogen generated with carbon monoxide or carbon dioxide under high pressure, the laser generating device comprising a plurality of laser rods containing a laser activating substance and adapted to condense and irradiate sunlight on the laser rods to generate radiant light from the laser rod by the action of the laser activating substance, and amplify and oscillate the radiant light, the semiconductor electrode being formed of a material having such properties as to absorb the laser beams generated in the laser generating device.

There is also provided a methane/methanol generating system which further comprises a wavelength adjusting member provided in a laser beam transmission path for converting or shifting the wavelength of the laser beams.

Either of the above two systems of the present invention can absorb the optical energy of sunlight to the maximum, produce hydrogen with this energy, and produce methane or methanol using the hydrogen thus produced. In order to maximally absorb the optical energy of sunlight with high efficiency, the laser generating device is kept stationary or goes around in space around the earth. The laser beams thus produced are transmitted from space through a relay device (including a reflecting mirror and a light amplifier) and received by a light-receiving facility (including a reflecting mirror and a condensing mirror) on land or on the sea. Thereafter, they are guided to the hydrogen generating unit and irradiated on its semiconductor electrode.

As the laser generating device, it is preferable to use a solid laser which is simple in structure and lightweight and is easy to select and set wavelengths of laser beams generated within a desired range. The laser generating device may comprise a sunlight-excited solid laser which comprises a condensing lens for condensing sunlight at high density and one or a plurality of elongated laser rods arranged in parallel at predetermined spacings, optical resonators comprising reflecting mirrors provided at both ends of the each laser rod, a light reflecting member surrounding the laser rods, sunlight condensed by the condensing mirror being irradiated on the laser rod or passed a plurality of times through the laser rod by reflecting by the reflecting mirror, thereby generating radial light in the laser rods by the action of the laser activating substance by amplifying and oscillating the radiant light by means of the optical resonator.

With such a solid laser, by adding various laser activating substances to the laser rods, it is possible to absorb solar energy within a wide wavelength range of sunlight and efficiently oscillate laser beams. In selecting the materials of the laser rod and the laser activating substance, it is necessary to select such materials that oscillate laser beams having such a wavelength that allows for efficiently transmitting the laser beams from space to the light-receiving facility on land or on the sea without reduction due to influences of scattering by air (Rayleigh scattering) or resonance absorbance.

As a wavelength of laser beams that is good in transmission efficiency, about 1 $\mu$m is the most suitable. But the limit on the short-wavelength side is about 500 nm. Lasers that meet these conditions include Nd-YAG laser and titanium sapphire laser. For an Nd-YAG laser, a desirable wavelength is 1.06 $\mu$m while for a titanium sapphire laser, it is 780 nm. These two lasers are suitable as solid lasers for transmitting laser beams to the earth.

In such Nd—YAG laser and titanium sapphire laser, laser activating substances such as Nd (neodymium) or Ti (titanium) are contained, and their sunlight absorbing wavelengths have a peak near e.g. 500 nm for titanium sapphire laser. If activating substances such as Ce (selenium) or Cr (chromium) are further added, optical energy of sunlight is absorbed with different absorbing wavelengths peculiar to the respective activating substances, so that sunlight can be absorbed over a wider wavelength area and the oscillating efficiency increases.

The laser beams transmitted from the solid laser of the materials selected to meet these conditions through space and efficiently received by a light-receiving facility are irradiated on the semiconductor electrode of the hydrogen generating unit to produce hydrogen. The hydrogen generating unit has a semiconductor electrode and a negative electrode arranged in two chambers of an electrolytic solution which are insulated from each other by a diaphragm and are filled with water with an electric circuit formed by connecting both electrodes through a load. Through a transmission window of the chamber in which is arranged the semiconductor electrode, laser beams are irradiated to produce electrical energy to decompose water. At the negative electrode, by the electrical energy generated, water is decomposed to produce hydrogen.

In order for the semiconductor electrode to have such a function, it is necessary to cause the wavelength of laser beams to match the absorbing wavelength of the semiconductor electrode by providing an electrode of such a material that the semiconductor electrode can absorb the laser beams transmitted, or irradiating laser beams having a wavelength converted or shifted to a wavelength which allows absorption by the material used for the semiconductor electrode. For example, if an Nd-YAG laser is used as the solid laser, the oscillating wavelength is 1.06 $\mu$m. If as the semiconductor electrode, P type indium phosphorus (P—InP) (which surface is coated with Rh, Pt or the like) is used, its absorbing wavelength is near 1 $\mu$m. Thus it is possible to directly irradiate a laser beams transmitted from space as it is.

If a titanium sapphire laser is used as the solid laser and titanium oxide ($TiO_2$) (to be precise, titanium oxide (IV) or titanium dioxide) is used as the semiconductor electrode, since the wavelength of the titanium sapphire laser is 780 nm, as in the second invention, laser beams of the above wavelength are converted to two-fold higher harmonic waves (390 nm) by the wavelength adjusting means in the transmission path and irradiated on the semiconductor electrode. Since the semiconductor electrode of titanium oxide absorbs short-wave laser beams over 400 nm (ultraviolet rays) well, even with laser beams of the above transmission wavelength, a combination can be made suitable by conversion of the wavelength. The wavelength adjusting means is a wavelength conversion means which converts to two-fold higher harmonic waves when light passes it. A material such as a KDP crystal is used.

If P type indium phosphorus is used as the semiconductor electrode, laser beams transmitted remain to have the oscillating wavelength. But the energy for electrolysis of water is insufficient. For efficient electrolysis of water, applying a bias voltage is preferable.

If laser beams of a predetermined wavelength are irradiated, electrons are excited beyond the forbidden band by optical energy in the semiconductor electrode of the hydrogen producing unit. Due to movement of electrons, water in contact with the semiconductor electrode is decomposed, so that oxygen is produced. At the same time, electric energy is produced between it and the negative electrode, which flows through a load, and on the cathode side, water is decomposed and hydrogen is produced. The hydrogen produced is supplied to the methane/methanol producing unit.

The methane/methanol producing unit is connected to a hydrogen discharge pipe of the hydrogen producing unit and also separately provided supply sources of carbon monoxide (CO) and carbon dioxide ($CO_2$) gas are connected to the methane/methanol producing unit. To the hydrogen discharge pipe, a pressurizing means (compressor) is provided, and in the passage from the CO or $CO_2$ supply sources, too, a pressurizing means is provided. Hydrogen and CO or $CO_2$ gases that have been pressurized to high pressure by the pressurizing means are reacted and synthesized in a high-pressure container to produce methane ($CH_4$) or methanol ($CH_3OH$).

As described above, methane and methanol can also be produced from methane hydrate. In such a method, carbon dioxide is produced during the producing steps. But in the generating system of this invention, since carbonic acid gas that already exists is used and the carbonic acid gas is used merely cyclically as a fuel, the content of carbonic acid gas will never increase in the atmosphere.

Other features and objects of the present invention will become apparent from the following description made with reference to the accompanying drawings, in which:

BRIEF DESCRIPTION OF THE DRAWINGS

FIG. 10 is a schematic view of a laser generating device of the methane/methanol generating system of a second embodiment;

DETAILED DESCRIPTION OF THE PREFERRED EMBODIMENTS

Figure 1:
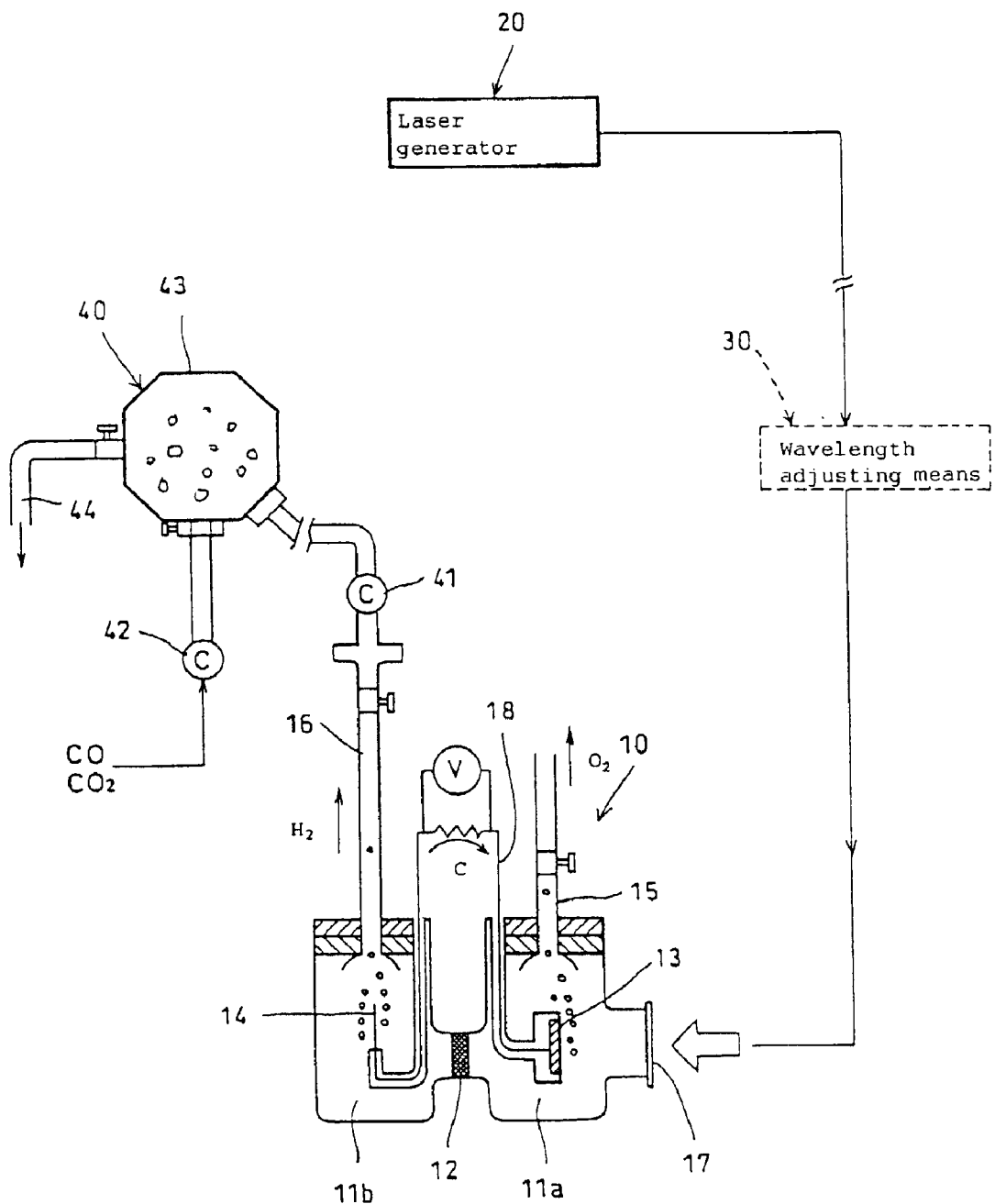
FIG. 1 is a schematic view of a methane/methanol generating system of a first embodiment.

Hereinbelow, the embodiments of this invention will be described with reference to the accompanying drawings. FIG. 1 is a schematic view of an embodiment of a methane or methanol producing system according to the present invention. It comprises a hydrogen generating unit 10, a laser generating device 20, a laser beams wavelength adjusting means 30, and a methane or methanol producing unit 40. The hydrogen producing unit 10 shows a known principle type for producing hydrogen and oxygen by irradiating sunlight. In this embodiment, it differs therefrom in that laser beams of a specific wavelength are irradiated. The wavelength adjusting means 30 may or may not be provided according to the combination of the wavelength of laser beams produced by the laser generating device 20 and the semiconductor electrode of the hydrogen generating unit 10.

The hydrogen generating unit 10 has two chambers 11a, 11b filled with water as an electrolytic solution and partitioned by an insulating member 12, and is provided with a photocatalysis electrode (e.g. titanium dioxide) 13 and a platinum electrode (Pt) 14 in the chambers 11a and 11b, respectively, with the electrodes connected together through a load (r). Each chamber is formed by a casing made of a predetermined metallic material and has its top closed by a lid plate. Through the lid plates, discharge pipes 15 and 16 are connected. The discharge pipes 15, 16 serve to discharge oxygen and hydrogen gas produced, respectively. At one end of the chamber 11a, a light transmission window 17 is provided. Light is irradiated so that after having transmitted through the transmission window 17, the light will reach the semiconductor electrode 13 and be absorbed. Electric power produced in a connecting line 18 may also be used to decompose water.

Figure 2:
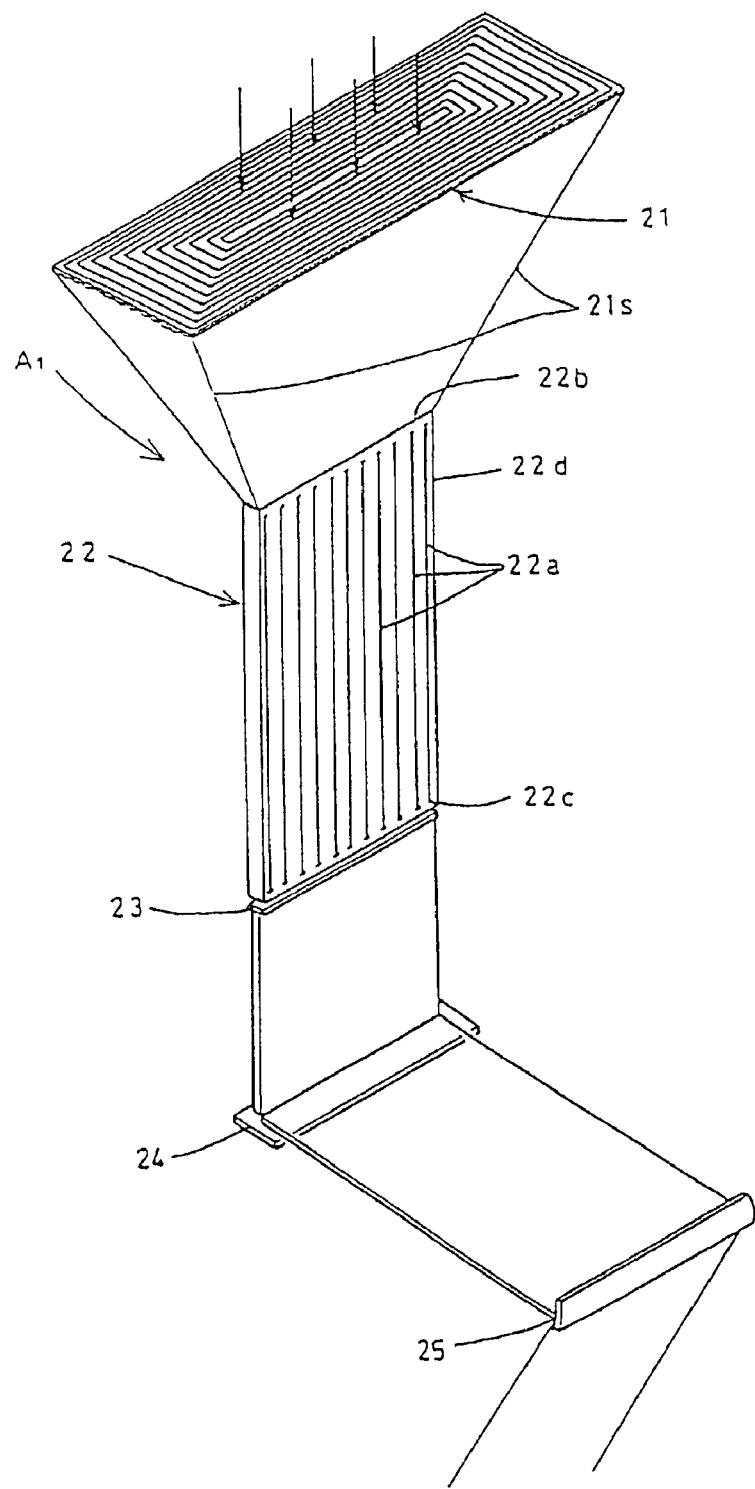
FIG. 2 is a schematic perspective view of a laser generating device.
Figure 3A:
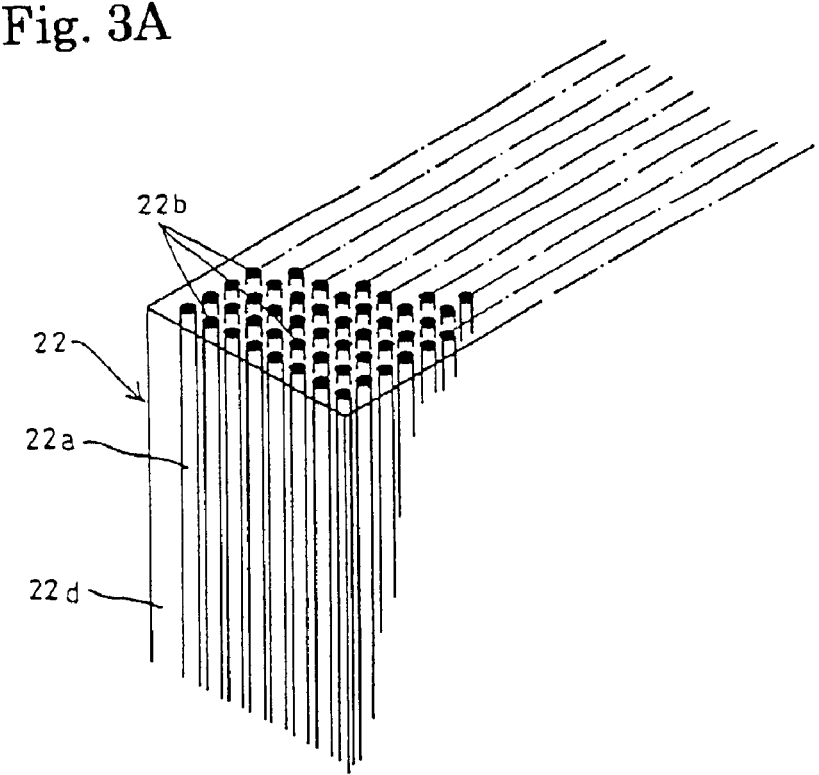
FIG. 3A is a partial enlarged perspective view of a solid laser generating portion.
Figure 3B:
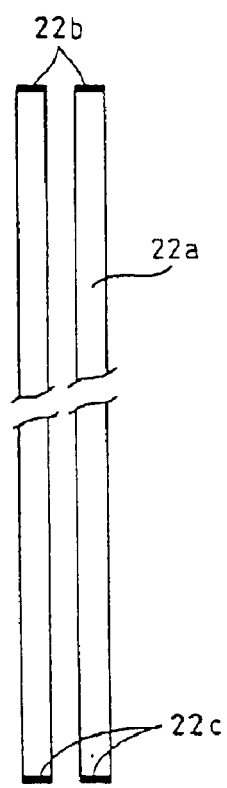
FIG. 3B is a partial sectional view of the same.
Figure 5A:
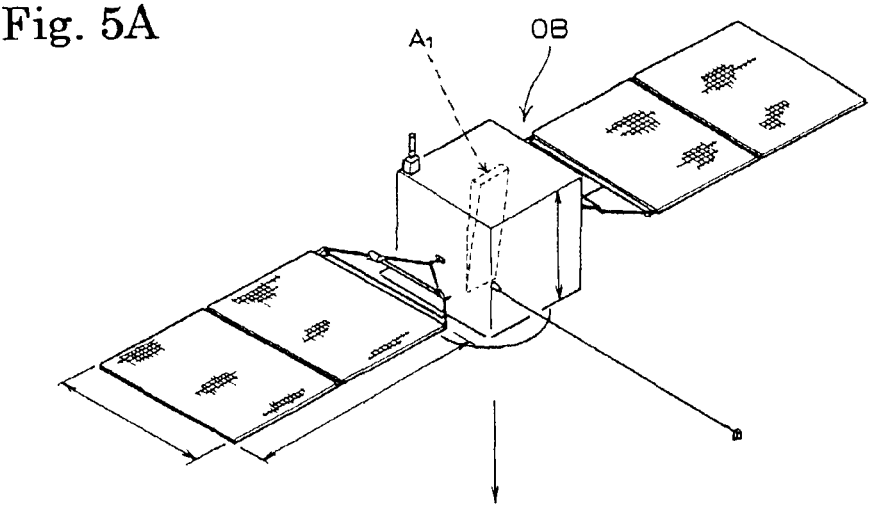
FIGS. 5A and 5B are schematic views of the solid laser generating device installed in an artificial satellite.
Figure 5B:
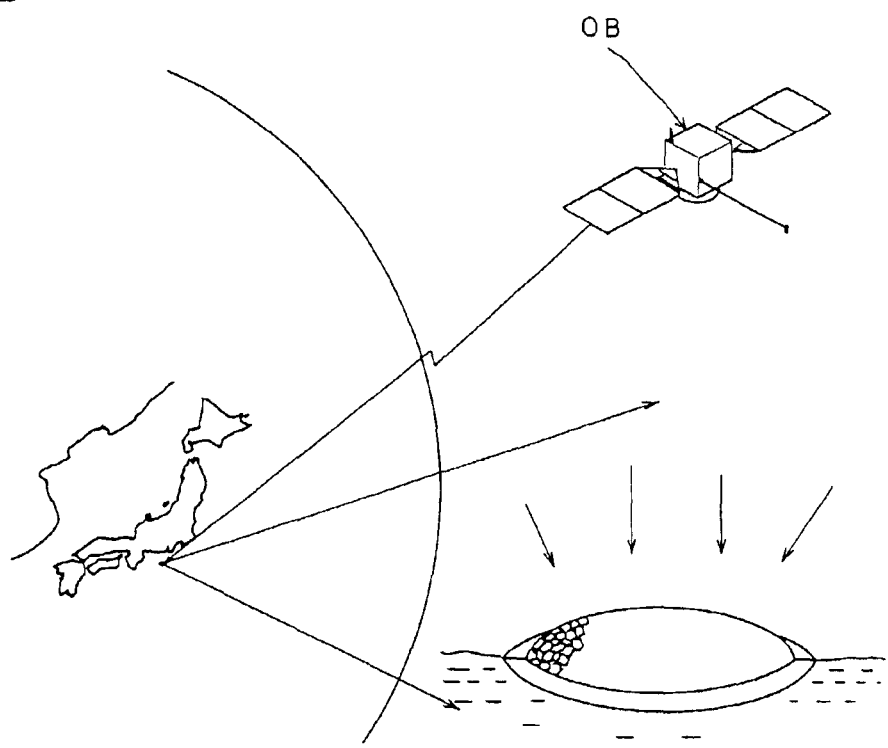

FIG. 2 shows a schematic view of the entire laser generating device. The sunlight-excited solid laser generating device A1 is installed, as shown in FIGS. 5A and 5B, in an artificial satellite OB that is stationary in space around the earth and is used to transmit laser beams to a specific location on the earth. This device A1 is provided with a Fresnel lens 21 for condensing sunlight as a condensing means, and a laser generating portion 22 provided thereunder. Laser beams generated are adjusted to be emitted parallelly through a holographic lens 23, and transmitted onto the earth through a reflecting mirror 24 and a condensing mirror 25. The holographic lens 23 does not necessarily have to be provided.

Figure 4A:
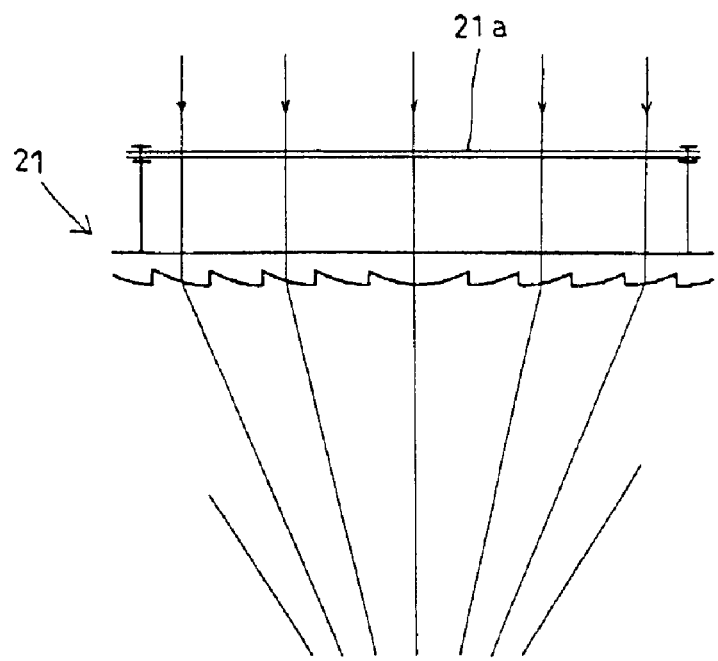
FIG. 4A is a partial sectional view of a Fresnel lens.
Figure 4B:
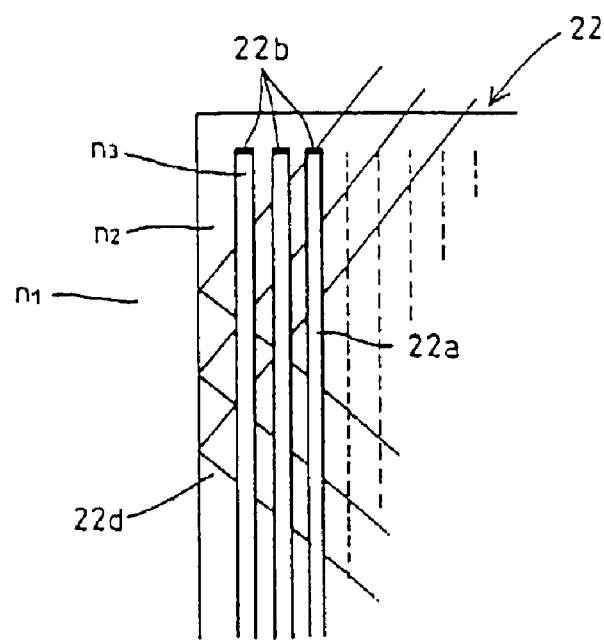
FIG. 4B is a partial sectional view of the laser generating portion.

The Fresnel lens 21 has a substantially rectangular light incident surface in this embodiment and is adapted to condense sunlight within a predetermined area in the center. As shown in FIG. 4A, rugged surfaces corresponding to the polarizing directions are formed on the emitting surface. The Fresnel lens 21 is mounted and supported on the laser generating portion 22 by a suitable support member 21s. Even if the thickness of the Fresnel lens 21 is 1 mm, it is possible to condense light. In the embodiment, if the thickness is 1 mm and a plastics having a specific weight of 1 is used, even for condensing solar power of 30 MW, its weight will be about 25 tons. For the shape of the Fresnel lens 21, besides that shown, various shapes are conceivable. For example, it may be columnar, square, etc. Also, a composite consisting of small plastic Fresnel lenses may be used.

The laser generating portion 22 is formed by arranging a plurality of elongated transparent laser rods 22a to which is added a laser activating material, parallel to each other at predetermined intervals. Reflecting mirrors 22b and 22c provided with reflective coatings are formed at both ends of each laser rod 22a. The assembly of the laser rods 22a is buried in a clad portion 22d.

Figure 8A:
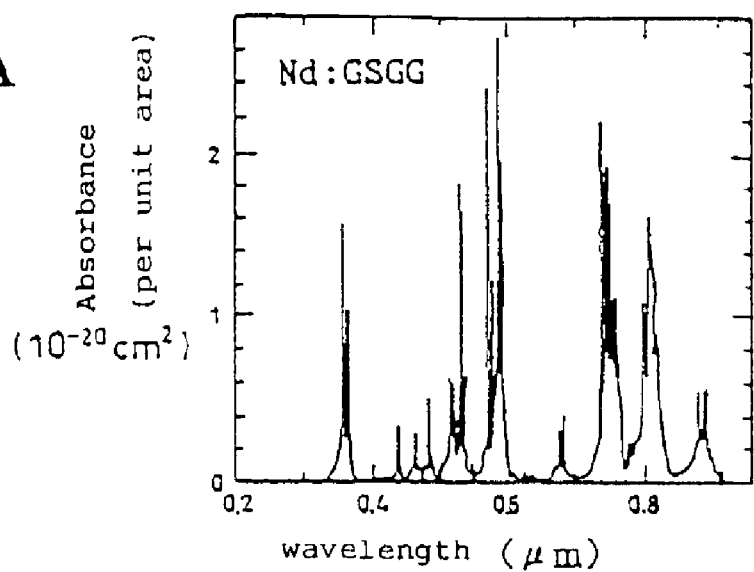
FIGS. 8A–8C are graphs showing the relation between the light absorbance of glass materials and the wavelength.
Figure 8B:
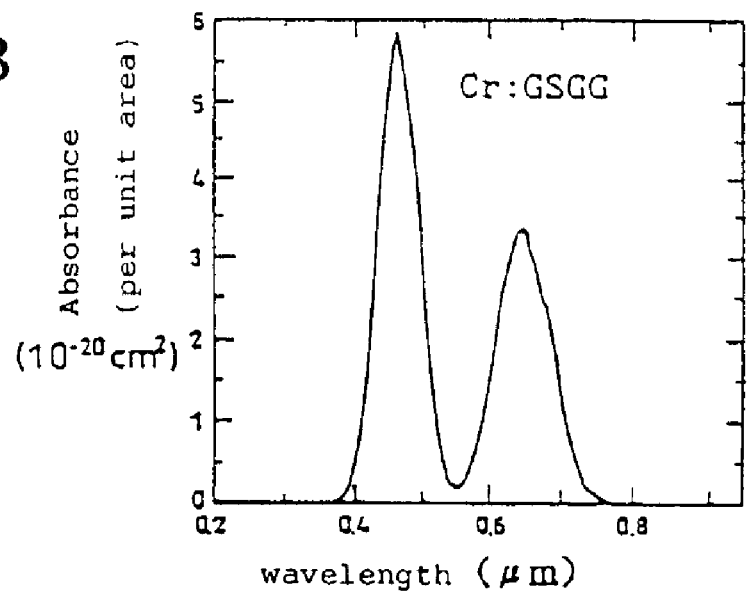
Figure 8C:
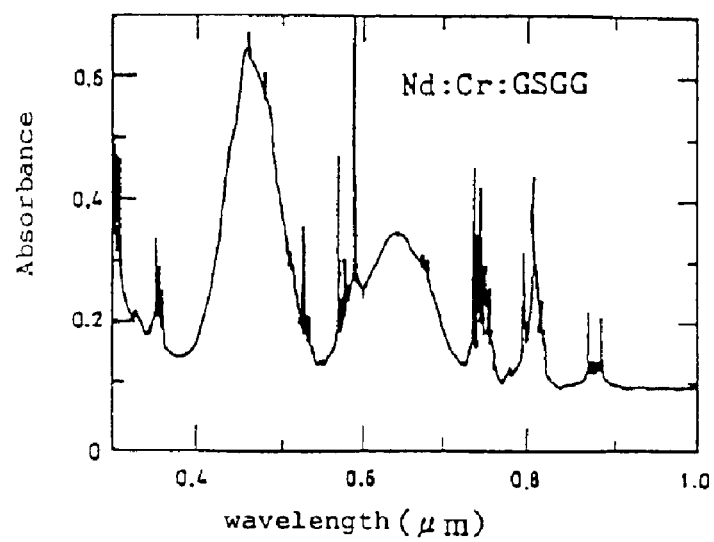
Figure 8D:
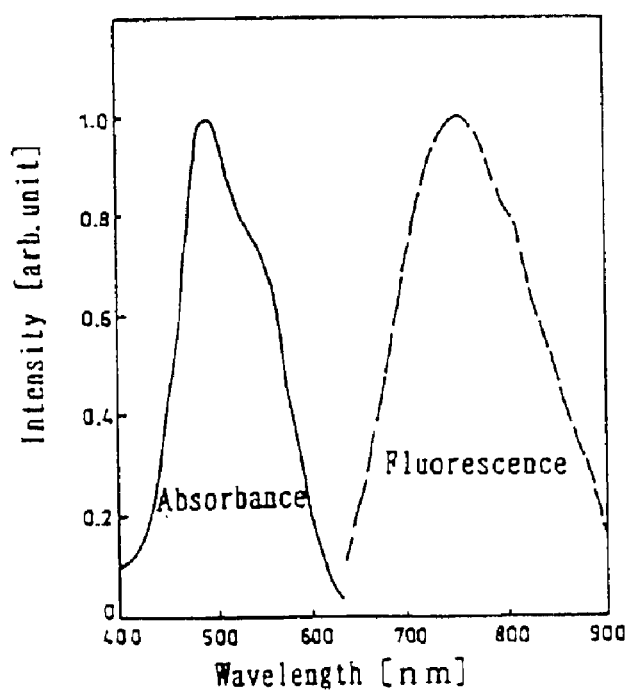
FIG. 8D is a graph showing a similar relationship of a titanium sapphire laser.

The elongated transparent laser rods 22a are several millimeters in diameter, and in the illustrated embodiment, 1 mm in diameter. For its material, glass, ceramic or a crystal may be used. As glass, a phosphate-family or a silicate-family material or the like is selected. For ceramic and crystal, Nd, Cr; GSGG, Nd; YLF, Nd; YAG, Yb; YAG or the like is selected. As a dopant to be added to the laser rods 22a, for example, Nd, Cr, Yb or the like is selected. As examples, wavelength-absorption characteristics when each of Nd and Cr is added in GSGG, and those when both Nd and Cr are added are shown in FIGS. 8A–8C. FIG. 8C shows that if both Nd and Cr are added, it becomes a material that has good absorption characteristics for wide wavelengths. FIG. 8D shows wavelength-absorption dependency for titanium. If Ti and Cr are added, most of the energy of the sunlight is absorbed by Nd, YAG crystal. They are added to glass or ceramics crystal in the form of ions.

The laser rods 22a have a length corresponding to the length of the clad portion 22d, and they are provided adjacent to each other at such predetermined distances from each other that $10^3$–$10^6$ pieces can be buried in the clad portion 22d. The volume occupying rate with respect to the clad portion 22d is about 1% or less. The reflecting mirrors 22b, 22c are provided at both ends of the laser rods 22a. The former 22b has a high-reflex coating of dielectric multilayered film having nearly 100% reluctance and the latter 22c has a reflex coating of about 80% reflectance (transmission rate 20%) to form an optical resonator.

The clad portion 22d comprises a rectangular plate having a thickness of 10 cm, a width of 10 meters and a length of about 20 meters in this embodiment, and a plastic or glass material (having a specific weight of about 1) doped with one or more rare-earth elements such as Nd, Yt, Ga, Cr, Ti is used. The actual clad portion 22d is formed by assembling split segments of about 1 meter in the width direction. Assembling is carried out in space.

The normal or holographic lens 23 is a kind of polarizing means for adjusting light parallelism to transport for a long distance. Since laser beams have a strong tendency to advance in a straight line and thus a small-diverging angle, according to the installation distance/position, it does not necessarily have to be provided. The reflecting mirror 24 is a flat-plate mirror which reflects laser beams, which are advancing in a straight line, to the condensing mirror 25 in parallel. On the reflective surfaces of the reflecting mirror 24 and the condensing mirror 25, reflective films are applied which have the highest reflectance suitable for the wavelength (1 μm) of laser beams generated.

Figure 7:
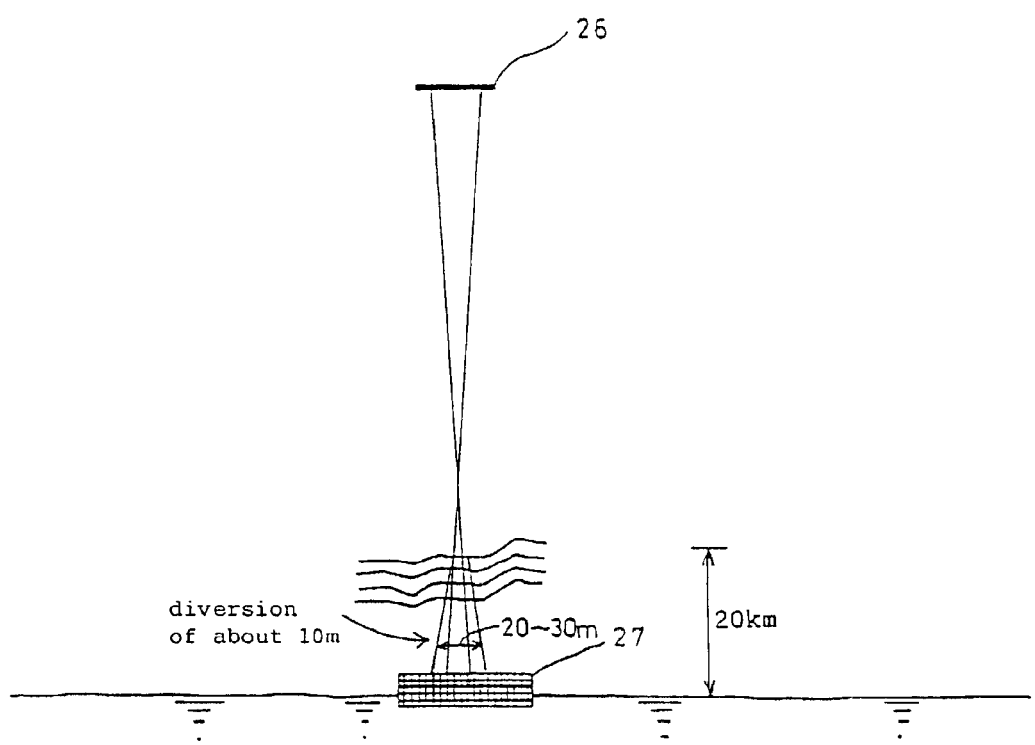
FIG. 7 is a schematic view of a the light-receiving facility.

Laser beams condensed by the condensing mirror 25 are emitted from the artificial satellite OB to the earth, and on their way, they may be relayed by a transmission mirror 26 shown in FIG. 7. The laser beams are received by a light-receiving means of a light-receiving facility provided on a megafloat 27 on the sea. The diameter of the transmission mirror 26 is 20 meters in this embodiment. The transmission mirror 26 also performs correction of wave fronts. The light-receiving means mainly comprises a reflecting mirror and a condensing mirror and transmits laser beams received to a hydrogen generating means.

The megafloat 27 is stationary on the sea. But it may be a movable ship considered as an alternative for a large aircraft carrier. The light-receiving means installed thereon is provided within a light-receiving area of several hundreds meters in diameter. In view of the fact that the reaching area of laser beams transmitted may move by several tens of meters laterally due to the influence of fluctuation of the atmosphere, an extra range of several tens of meters is preferably added to the several hundreds-meter-diameter light-receiving range.

Even if it is not the megafloat 27 or a movable ship, it is possible to receive light by means of a light-receiving facility fixed on land. Also, while not shown, in a light path of laser beams transmitted from the condensing mirror 25 to the transmission mirror 26, a plurality of sets of relay mirrors may be provided.

With the sunlight-excited solid laser generating device A1 of this structure, laser beams are generated at high efficiency by directly exciting the laser generating portion 22 with sunlight. Sunlight condensed by the Fresnel lens 21 is irradiated from various oblique directions into the plurality of laser rods 22a from the top end of the laser generating portion 22. Light entered into one laser rod 22a is partially absorbed and passes therethrough to adjacent laser rods 22a one after another. Any light not absorbed by the laser rods 22a is reflected by the outer end of the clad portion 22d, advances in the opposite direction and is further absorbed by the transparent laser rods 22a.

Sunlight entered into the laser rods 22a acts on the laser activating substance in the laser rods to excite radiant light, which reciprocates many times between the reflecting mirrors 22b and 22c at both ends of the laser rods 22a and is gradually amplified. When it exceeds a predetermined level, it is emitted from the reflecting mirror 22c on the outlet side. Laser beams are thus obtained. The laser beams obtained have their flux directivity adjusted in order by the holographic lens 23 and are emitted from the condensing mirror 25 and received by the light-receiving facility on the earth. Since the ultraviolet-blue area and infrared area of sunlight are unnecessary for laser excitation or harmful to optical elements or produce excess heat, they may be removed by an optical filter 21a.

The laser beams thus obtained are, in this embodiment, near-infrared light having a wavelength of about 1 μm. The energy converting efficiency of the laser beams obtained is more than 30%. Its breakdown is as follows.

Absorbance of sunlight: 0.7 (effective wavelength area: 0.4–0.9 μm)

Laser efficiency: 0.6

If such a sunlight-excited solid laser generating device is used, the laser output per one unit will be 10 MW. This is the laser output obtained by condensing a sunlight power of 35 MW with a Fresnel lens corresponding to an area of $2.5 \times 10^4$ $m^2$ (corresponding to 160 square meters) and entering it into the clad portion 22d having a sectional area of 1 square meter. The sunlight power is the power obtained when the energy of 1.3 kw per square meter received from the sun by an artificial satellite kept stationary in space at 36000 km from the earth is received by a Fresnel lens.

The output of each laser rod of the laser generating portion 22 is in the order of 10 kw to 10 Mw. The length of the resonance of laser beams oscillated by the optical resonators provided at both ends of each laser rod is 200 meters (=20 meter×5×2) if they are oscillated by five circulations, and the angle divergence of light permitted for laser rods of 1 mm diameter is about $0.5 \times 10^{-5}$ rad. Natural divergence at about 4000 km ahead is about 200 meters (=$0.5 \times 10^5 \times 40000 \times 10^3$). That is to say, by providing a light-receiving means within a range of 100 meters, it is possible to receive light energy.

This is possible by setting the aspect ratio, which is the ratio between the diameter and length of the laser rods, equal to or greater than the above predetermined value, thereby suppressing the diverging angle of laser beams. This is an advantage inherent to the structure of a laser generating device using elongated laser rods. With the burning threshold value of a currently available light-receiving means, it is said that receiving laser beams from a laser generating device (per unit) within the range of 100 meters is a limit. But if the limit value of the light-receiving means improves, it is possible to further reduce the light-receiving range on the earth. In this case, for example, if they are adapted to be oscillated after 20 reciprocations, divergence will decrease to ¼ or about 50 meters, so that by providing a converging mirror on the way, the diameter on the earth can be reduced to about 10 meters.

As shown in FIG. 7, since laser beams begin to be influenced by atmospheric turbulence at around 20 km above the ground, fluctuation of about 10 meters can develop in laser beams that are transmitted to the earth. Thus, the light-receiving means on the megafloat 27 may be provided within an area range of about 20–30 meters. The thus transmitted laser beams is near-infrared light having a wavelength of 1 μm. With this wavelength, since it is out of the resonant level of vapor, laser beams are transmitted to the earth without being affected by the existence of the atmosphere.

For use of laser beams transmitted from one unit of solid laser generating device A1 on the ground, the number of units should be 150 in view of cost performance. If 150 units of the solid laser generating device A1 are shot up, the total weight of parts shot up will be as follows.

The weight of the Fresnel lens 21 of 2.5 tons per unit is determined taking into consideration the structure of a support portion. The laser generating portion 22 is about 2 tons per unit. Thus 150 units will weigh about 300 tons. The reflecting mirror, condensing mirror and transmission mirror including driving devices will weigh about 10 tons. For 150 units, about 300 of them axe needed (thus weighing 3000 tons). After all, the weights are roughly as follows.

Fresnel lens portion: 375×N (support portion weight)
Solid laser portion: 300 tons
Transmission mirrors: 3000 tons
Total weight: 6000 tons (N=10) (for 150 units)

Laser beams thus generated by the laser generating devices $A_1$ installed as described above are irradiated on the hydrogen generating unit 10. Hydrogen generated is supplied to the methane or methanol producing unit 40 connected through the hydrogen discharge pipe 16, where it is converted to methane or methanol, as will be described later.

Figure 6:
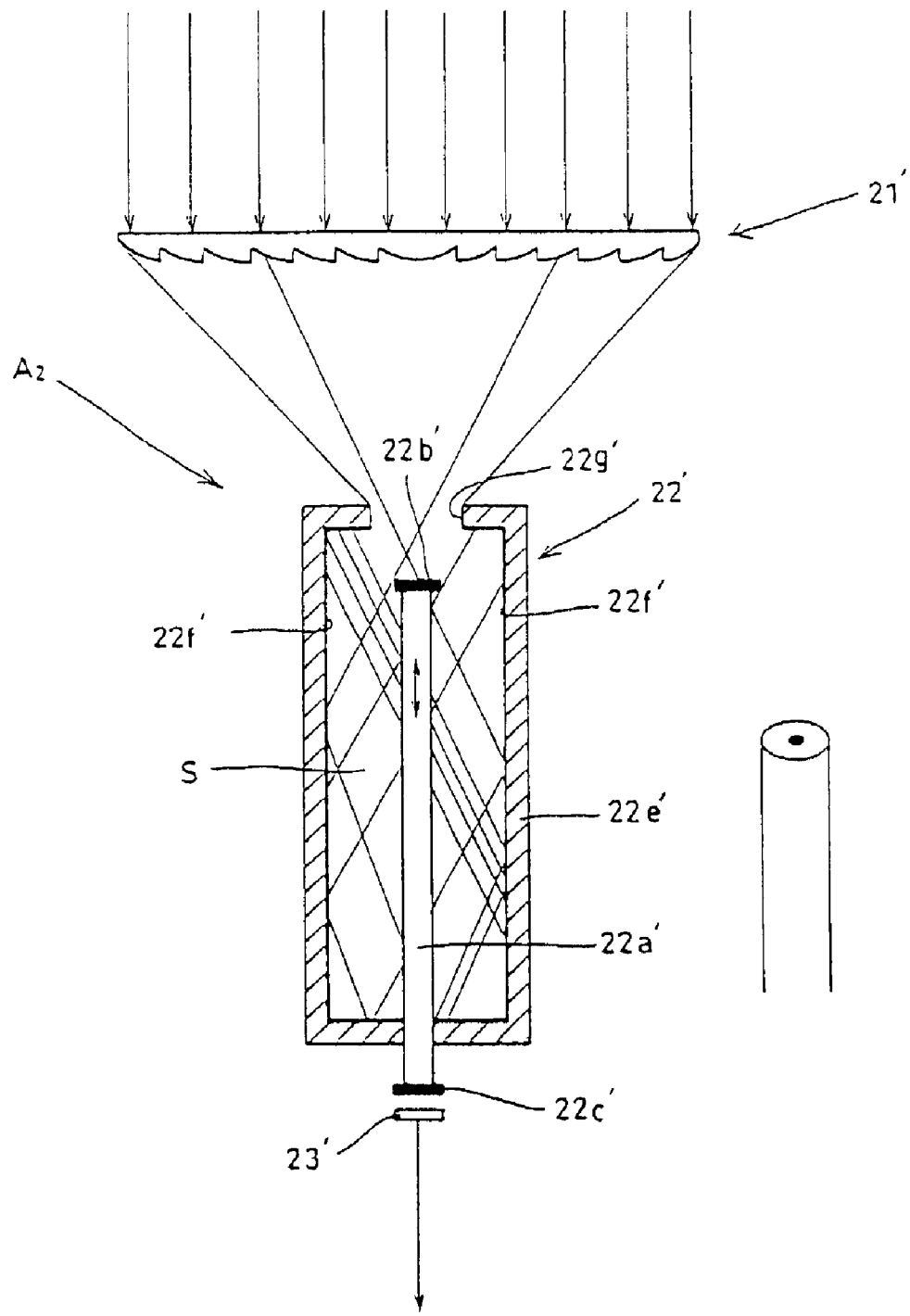
FIG. 6 is a schematic view of a modified embodiment of the laser generating device.

FIG. 6 shows the structure of a modified embodiment of a sunlight-excited solid laser generating device A2. While a Fresnel lens 21' as a condensing means is similar to that in the first embodiment, its structure slightly differs in that the shape is concentric and that no clad member is provided in the laser generating portion 22'. The laser generating portion 22 ' is provided with a single elongated laser rod 22a' in a metallic cylindrical hollow cavity 22e', and optical resonators of reflecting mirrors 22b', 22c' at both ends of the laser rod 22a'.

The laser rod 22a' is formed of glass or crystal as in the first embodiment, and as a laser activating substance, Nd and/or Cr is contained. The space S in the cylindrical hollow cavity 22e' around the laser rod 22a' is in vacuum, and the inner surface of the hollow cavity 22e' is formed as a reflective surface 22f' to which is applied a coating having a high reflectance of nearly 100%. Sunlight introduced through an opening 22g' formed at the top end of the cavity 22e' is irradiated on the laser rod 22a' directly or after being reflected by the reflective surface 22f' to generate radiant light by the action of the laser activating substance in the laser rod 22a'. After being oscillated by reciprocating a plurality of times between the optical resonators at both ends of the rod, laser beams are entitled from the reflecting mirror 22c' at the output side.

In the illustrated embodiment, the laser rod 22a' is a single solid rod, but may be formed of a plurality of rods. In this case, the reflecting mirrors 22b' and 22c' are provided at both ends of each rod. The reflecting mirrors 22b' and 22c' are the same as used in the first embodiment. The one reflecting mirror 22b' has a reflective surface provided with a dielectric multilayered coating having a high reflectance of nearly 100%, or a metal-coated reflective surface. The other reflecting mirror 22c' at the output side has a reflective surface provided with a coating having a reflectance of about 80% (transmission rate 20%). The laser rod 22a' has substantially the same length as the cavity 22e', but has its bottom end slightly protruding downwardly from the bottom of the cavity 22e'.

Also, while not shown, the clad layer may be provided in two or three layers around the laser rod 22a'. The clad layer is formed by laminating the same clad material as used in the first embodiment in layers. Even if the outer diameter of the clad layer increases, at least the vacuum space S must remain. Generally, the clad layer is preferably in thin layers. The clad layer is provided to ensure a maximum incident rate because a laser rod 22a' made of glass reflects light on its surface, so that sunlight cannot enter into the rod. By two or three clad layers having different refractive indexes, the refractive index is adjusted so that the incident rate will be maximum.

The operation of the solid laser generating device A2 is basically the same as in the first embodiment, and it is also the same in that it is installed in an artificial satellite that is stationary at a predetermined distance from the earth. When sunlight condensed by the Fresnel lens 21' is radiated obliquely through the opening 22g' of the cylindrical cavity 22e', the sunlight is irradiated on the laser rod 22a' directly or after being reflected on the reflective surface 22f', and part of it is taken into the rod. Sunlight that has passed through the laser rod 22a' is reflected by the reflective surface 22f' and repeatedly entered into the laser rod 22a' and taken into the rod.

The sunlight acts as pumping light, so that emission is induced in the laser rod 22a' by the action of the laser activating substance and is gradually amplified while making round trips between the reflecting mirrors 22b' and 22c'. When laser beams reach a predetermined level or over, they are outputted from the reflecting mirror 22c' at the output side. The laser beams thus obtained are transmitted to the earth by the reflecting mirror 24 and the condensing mirror 25 as in the first embodiment.

Figure 9:
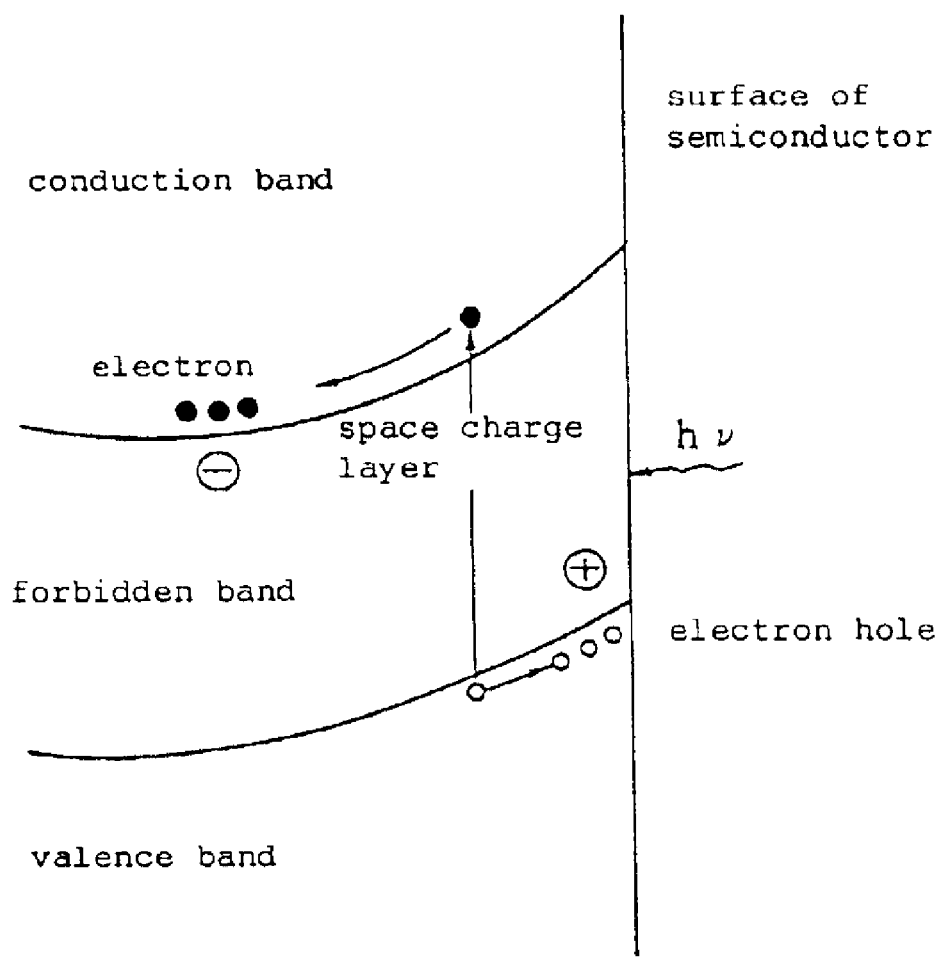
FIG. 9 is a view for explaining the operation of a semiconductor electrode.

As described above, the laser generating devices A1, A2 of the first and second embodiments are combined with the hydrogen generating unit 10, and the laser beams generated are transmitted from space and irradiated on the semiconductor electrode 13 of the hydrogen generating unit 10. As shown in FIG. 9, when the laser beams are irradiated, the semiconductor electrode 13 absorbs the laser beams and electrons in the semiconductor are excited beyond the forbidden band in the electrode 13.

In the illustrated embodiment, the semiconductor electrode is made of P type indium phosphorus and its light-absorbing wavelength is about 1 μm. On the other hand, since the wavelength of laser beams oscillated by the solid laser generating devices A1 and A2 of the two embodiments is also about 1 μm, the wavelength of laser beams transmitted from space matches the absorbing wavelength of the semiconductor electrode. Thus, they are directly irradiated on the semiconductor electrode not through the wavelength adjusting means 30. Also it is possible to produce hydrogen efficiently by applying a bias to them.

When the laser beams are irradiated on the semiconductor electrode 13, electrons excited in the conduction band of the semiconductor electrode 13 flow to the platinum electrode 14 through a load. This movement of electrons decomposes water in contact with the semiconductor electrode 13, so that oxygen ($O_2$) is produced as gas. On the other hand, at the platinum electrode 14, hydrogen ($H_2$) is produced as gas by decomposition of water. Light may be irradiated from below or the surface may be scanned to avoid the influence of hydrogen produced.

The reactions are extremely simple ones that follow the process shown by the following formulas.

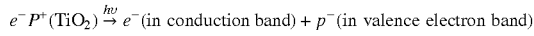

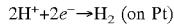

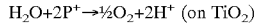

The hydrogen discharge pipe 16 of the hydrogen generating unit 10 is connected to the methane/methanol generating unit 40 where methane or methanol is produced. As shown in FIG. 1, the methane or methanol generating unit 40 is of a known structure. It is formed by connecting a high pressure generating compressor 41 as a high pressure generating means for pressurizing hydrogen supplied from the unit 10 to a high pressure, and a compressor 42 for pressurizing CO or $CO_2$ supplied from a supply means (not shown, such as a steam power plant) to a high-pressure container 43. In the methane or methanol generating unit 40, high-pressure hydrogen and CO or $CO_2$ pressurized to a high pressure are synthesized under high pressure in the high-pressure container 43, and methane (gas) or methanol (liquid) is produced. Methane or methanol is produced with the mixing ratio of hydrogen and CO, $CO_2$ set at a ratio suitable for synthesis of methane or methanol. The synthesizing reaction is carried out following the reaction formulas indicated in the prior art section. 44 is a discharge pipe.

Figure 11A:
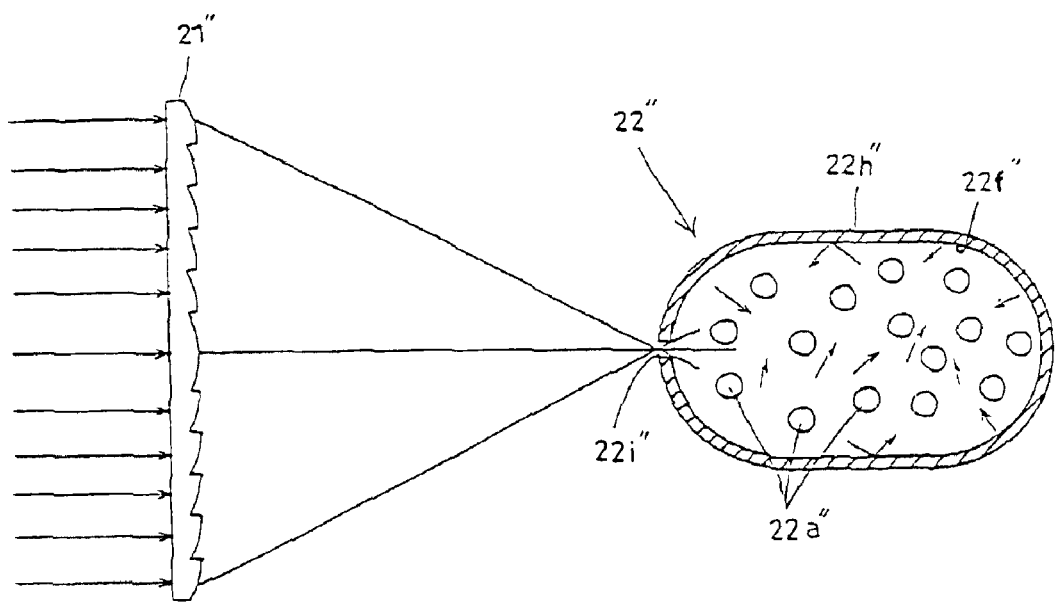
FIG. 11A is a side view of the same.
Figure 11B:
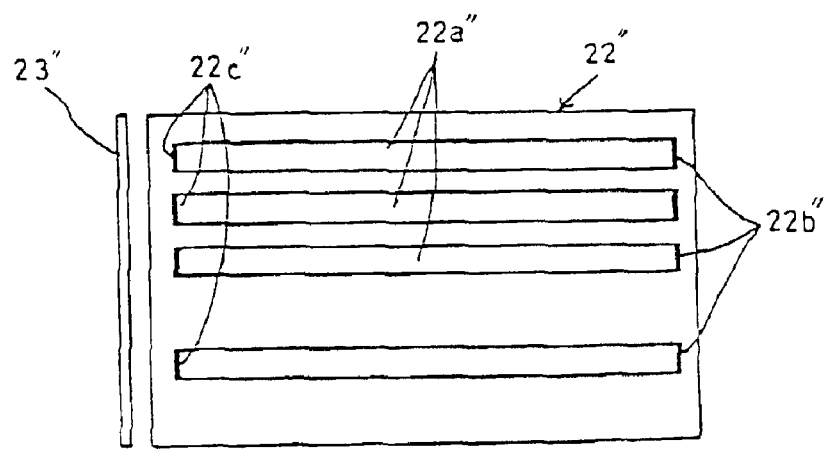
FIG. 11B is a partial plan view of the same.
Figure 12:
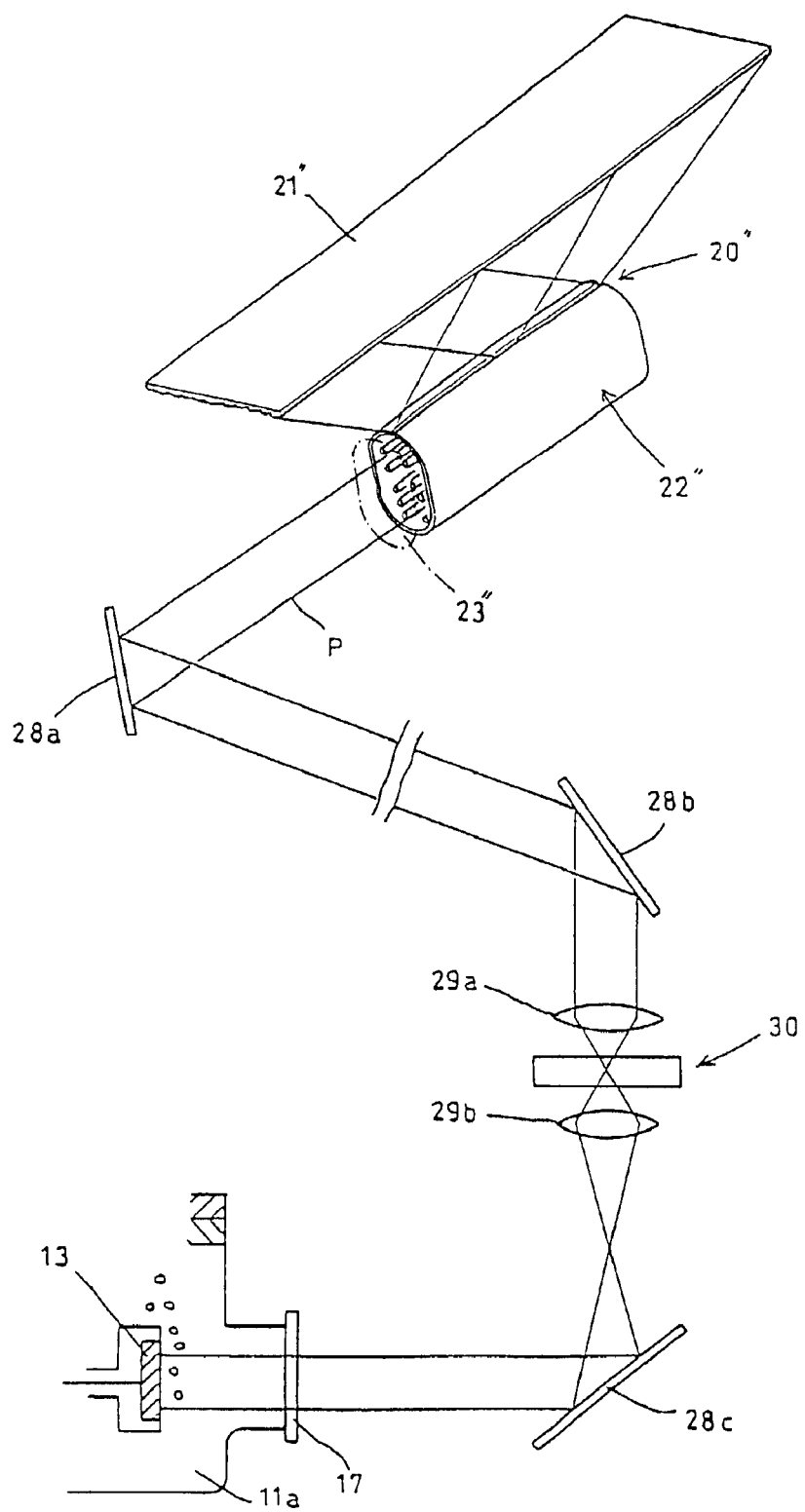
FIG. 12 is a schematic view of a laser beam transmission system.

FIGS. 10–12 show a schematic structure of a laser generating device 20" used for the methane/methanol producing device of a second embodiment. As in the first embodiment, the laser generating device 20" is also installed in an artificial satellite which is stationary in space around the earth or is rounding it, and transmits laser beams to a specific location on the earth. The laser generating device 20" is provided with a Fresnel lens 21" for condensing sunlight as a condensing means, and a laser generating portion 22" provided corresponding thereto.

Although this embodiment differs from the first embodiment in that the laser generating device 20" uses a wavelength adjusting means 30, and a different material is used for the semiconductor electrode of the hydrogen generating unit, the overall structure is the same as in the first embodiment. Thus for the same functional members, description is omitted, and description will be made mainly on the laser generating device 20". In this embodiment, as the semiconductor electrode, titanium oxide ($TiO_2$) (To be precise, it is called titanium oxide (IV) or titanium dioxide. Hereinbelow, abbreviated) is used.

For the laser generating portion 22", a plurality of elongated transparent laser rods 22a" coated with a laser activating substance are arranged at predetermined intervals and in parallel to each other in a casing 22h". Reflective coatings are applied to both ends of each laser rod 22a" to form reflecting mirrors 22b" and 22c". Light is introduced through a window 22i". On the inner surface 22f" of the casing 22h", too, a reflective coating is applied. On the reflecting mirror 22b" and the inner surface 22f" of the casing 22h", high reflective coatings of dielectric multilayered film having a reflectance of nearly 100% are provided. On the reflecting mirror 22c", a reflective coating having a reflectance of about 80% (transmittance 20%) is provided. The reflecting mirrors 22b" and 22c" form an optical resonator. The reflecting mirror 22c" is an output mirror.

The laser rods 22a" are several millimeters in diameter and 1 mm in the illustrated embodiment. For its material, in this embodiment, sapphire crystal is used. As a dopant added, for example, titanium is used. The laser rods 22a" are of a length corresponding to the length of the laser generating portion, and are about 5 mm in the illustrated embodiment. The plurality (e.g. ten) of laser rods 22a" are provided adjacent to each other at predetermined intervals. Laser beams oscillated by the laser rods 22a" are emitted after leaving the reflecting mirror 22c" and having parallelism of light adjusted by a holographic lens 23".

In the laser generating device 20", sunlight is condensed by the Fresnel lens 21" in space and introduced through the window 22i" and laser beams are excited and generated in the laser generating portion 22". Light introduced through the window 22i" extending along the entire length of the casing 22h" is reflected by the reflective surface of the inner surface 22f" in the casing 22h", hits many times on the laser rods 22a" and is absorbed by the laser rods 22a" every time it hits them. By the excitation of sunlight, radiant light is excited in the laser rods 22a", which reciprocates many times between the reflecting mirrors 22b" and 22c" as the optical resonator, and is gradually amplified and outputted from the reflecting mirror 22c" on the output side as laser beams P.

The laser beams (wavelength: 780 nm) are sent to the earth by the reflecting mirrors 28a and 28b and converted to two-fold higher harmonic waves by the wavelength adjusting means 30. The generating efficiency of laser beams generated by the laser generating device 20" is as high as about 80%, and the generating efficiency at which hydrogen/electric energy is generated in the hydrogen generating unit 10 using these laser beams is extremely high. Heretofore, when sunlight is directly irradiated, if titanium oxide ($TiO_2$) is used as the material for the semiconductor electrode 13, the efficiency was only about 1% at the most, and even if a material other than titanium oxide was used, it was about 2% at the most. Compared to this, the efficiency is much higher.

Since the illustrated laser generating device 20" is installed in space around the earth, laser beams from this device 20" are, as shown in FIG. 12, transmitted to the earth through the reflecting mirror 28a, which is installed at a space station on the way to the earth, and the reflecting mirror 28b, which is installed at a position near land or sea, and the wavelength is converted or shifted by the wavelength adjusting means 30 provided between the condensing lenses 29a and 29b.

For the wavelength adjusting means 30, a nonlinear optical element e.g. a KDP crystal board is used. Particularly in this embodiment, the wavelength of laser beams is converted to a half wavelength by an optical element for generating two-fold higher harmonic waves. Further, the converted laser beams are reflected by the reflecting mirror 28c and sent to the transmission window 17 of the hydrogen generating portion 10. If they are passed through the wavelength adjusting means 30, the higher the laser power density, the better the efficiency. Thus, light may converge. In order to avoid thermal deformation, light is preferably scanned using a large crystal or the crystal is moved at a high speed. As described later, the wavelength adjusting means 30 may be a member that shifts by a predetermined wavelength.

When laser beams transmitted from the laser generating device 20" are irradiated on the hydrogen generating unit 10, as in the first embodiment, the semiconductor electrode 13 absorbs the laser beams, so that electrons in the semiconductor are excited beyond the forbidden band in the electrode 13. In this embodiment, the semiconductor electrode is made of titanium oxide ($TiO_2$) which requires photons having an energy of 3 eV or over in terms of band gap Eg, which corresponds to light of 410 mm.

Figure 13:
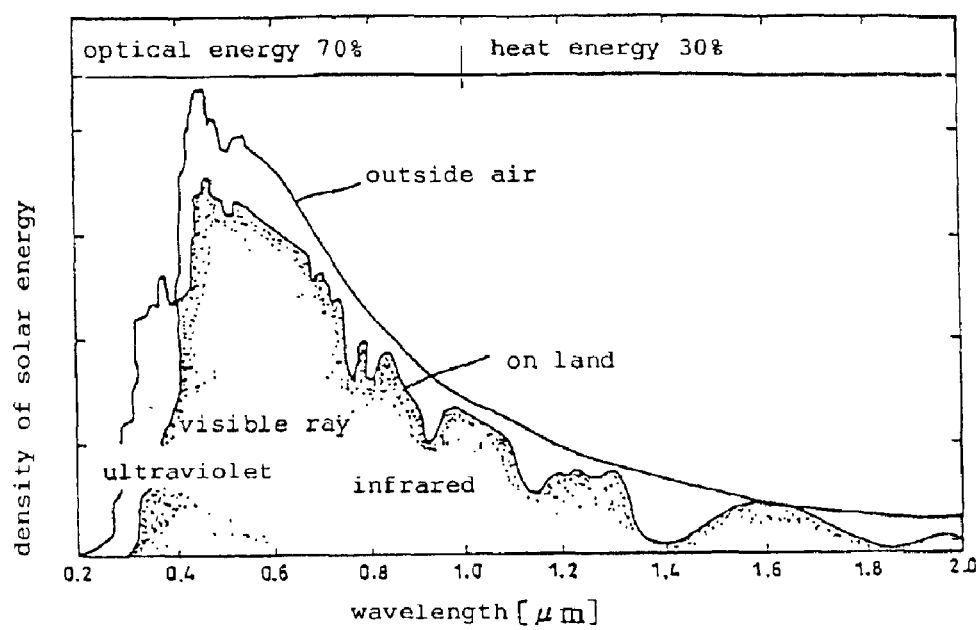
FIG. 13 is a spectrum distribution view of the energy density of sunlight.

Generally, in the spectrum of sunlight, as shown in FIG. 13, the energy density is the largest near the wavelength of 500 nm and the wavelength components at 400 nm or under are extremely few. Thus, even if sunlight is directly irradiated, the efficiency is extremely bad in a material of $TiO_2$. Thus although titanium oxide is inexpensive, practicality is low. Thus, in this embodiment, laser beams generated in the laser generating device 20″ have wavelength converted by the wavelength adjusting means 30 to a wavelength at which titanium oxide can absorb, and are irradiated through the transmission window 17 of the hydrogen generating unit 10 to produce a photochemical reaction.

For the laser generating device 20″, a titanium sapphire laser is used. Its light absorption-light emitting property is as shown in FIG. 8D. As is apparent from the figure, the titanium sapphire laser has the peak wavelength for light absorbance at about 500 nm. Thus it well coincides with the wavelength of the peak of the energy density of sunlight. Thus, sunlight is used for excitation with good efficiency, so that the light emitting efficiency increases. Since the oscillating wavelength of this laser is 780 nm, when it is converted to its two-fold higher harmonic waves by the wavelength adjusting means 30, laser beams of 390 nm are directly obtained from sunlight with good efficiency.

The laser beams with a wavelength of 390 nm are ultraviolet light, which acts on the semiconductor electrode 13 of titanium oxide ($TiO_2$) of the hydrogen generating unit 10 to produce a current. They can efficiently produce hydrogen by decomposing water with the platinum electrode 14.

Also, for the laser generating device 20″, a solid laser in which its laser rods 22a″ are formed of a material of which the major component is a sapphire crystal is cited for example. But as the laser, other lasers of various types can be used. For example, a sunlight-excited Nd—YAG glass laser (oscillating wavelength: 1.06 $\mu$m) installed in space may be used.

Also, for the material of the semiconductor electrode 13 of the hydrogen energy generating unit 10, too, besides titanium oxide, various ones may be combined. For example, there are P type indium phosphorus (P—InP) (surface coating of Rh, Pt, etc.: but external voltage has to be applied) (absorbing wavelength: about 1 $\mu$m ), and $FeS_2$ and $WSe_2$ which are shorter in absorbing wavelength and have an intermediate absorbing wavelength with titanium oxide. Also, a voltage may be additionally applied to the electrode as an auxiliary means to improve the generating efficiency.

Combinations of these laser generating devices 20 and 20″ and the semiconductor electrode 13 are as follows:

(1) Irradiated oscillated laser beams directly on the semiconductor electrode 13

If as the semiconductor electrode 13, P type indium phosphorus (P—InP) is used, and as the laser generating device 20, 20″, a laser which oscillates at a long wavelength such as an Nd-YAG laser, namely an Nd-YAG laser is combined with the semiconductor electrode 13 of P type indium, since the wavelength of the oscillated laser beams and the absorbing wavelength of the semiconductor electrode coincide with each other at around 1 $\mu$m, there is no need to convert or shift laser beams in the transmission path. Thus it is possible to utilize directly irradiated laser beams to excite the semiconductor electrode not through the wavelength adjusting means 30. Thus, in this case, the wavelength adjusting means 30 is not provided.

(2) Irradiating oscillated laser beams on the semiconductor electrode 13 after shifting them by a predetermined wavelength.

If for the semiconductor electrode 13, a material that is long in absorbing wavelength, such as P type indium phosphorus is used, and for the laser generating device 20, 20″, a laser that oscillates at a longer wavelength (1.2 $\mu$m) such as a Yb solid laser is used, oscillated laser beams are irradiated after having their wavelength shifted to around 1 $\mu$m, which is the absorbing wavelength of the semiconductor electrode 13, by the wavelength adjusting means 30. In such a combination, the same is true for the case in which the material of the semiconductor electrode 13 is of an absorbing wavelength shorter than that of P type indium phosphorus and the oscillated laser beams are slightly displaced.

In this combination, as the wavelength adjusting means, means for shifting the wavelength of laser beams by a predetermined wavelength is used. As such means, for example, optical fibers of a predetermined diameter and length are used in which transmitted laser beams are passed. Namely, optical fibers are used as a dielectric medium to develop induced Raman scattering to shift the original wavelength by a predetermined wavelength. Also, four-wave mixing means or an optical parametric oscillating means (OPO) may be used.

(3) Irradiating oscillated laser beams on the semiconductor electrode 13 after converting them to two-fold or three-fold higher harmonic waves.

In this case, it is as described in the embodiments in detail. If the semiconductor electrode of a short wavelength range such as titanium oxide (absorbing wavelength: 0.4 $\mu$m) is combined with the laser generating device 20, 20″, which generates two-fold or three-fold short-wavelength laser, laser beams are irradiated after being converted by the wavelength adjusting means to higher harmonic waves that are e.g. twice or three times the oscillated wavelength. Such a combination is also not limited to the above embodiments.

If a solid laser is used, the laser activating substance to be added to the laser rods is preferably at least one kind or more. It is preferable to employ a laser that absorbs over the entire wavelength over which the optical energy of sunlight is distributed. The more kinds of laser activating substances, the more optical energy of sunlight it is possible to absorb, and thus the higher the efficiency of the laser oscillation.

As described above, according to this invention, a laser generating device for absorbing optical energy of sunlight is installed in space, generated laser beams are sent onto land or sea, a hydrogen generating unit having a semiconductor electrode for generating hydrogen and a methane or methanol generating means for generating methane or methanol from the hydrogen produced are combined, the laser beams transmitted are irradiated on the hydrogen generating means, the laser beams irradiate on the semiconductor electrode are converted or shifted to the absorbing wavelength of the electrode or a wavelength which becomes the absorbing wavelength, and methane or methanol is produced from the hydrogen. Thus, most of the laser beams irradiated are absorbed by the semiconductor electrode, so that it is possible to use most of the optical energy of sunlight. Thus, a remarkable effect is achieved. Namely hydrogen is produced with extremely high efficiency and methane or methanol can be produced.

What is claimed is:

1. A methane/methanol producing system comprising a laser generating device configured to be installed in space around the earth for generating laser beams by sunlight and transmitting the laser beams generated to a predetermined position on land or on the sea, a hydrogen generating unit comprising a semiconductor electrode for receiving the laser beams and generating hydrogen, said semiconductor electrode configured to be irradiated with the laser beams to generate hydrogen by decomposition of water, and a methanol producing unit for producing methane or methanol by synthesizing the hydrogen generated with carbon monoxide or carbon dioxide under high pressure, said laser generating device comprising a plurality of laser rods configured to contain a laser activating substance, said laser generating device adapted to condense and pass sunlight onto said laser rods to generate radiant light from said laser rods by the action of said laser activating substance, and amplify and oscillate the radiant light, said semiconductor electrode being formed of a material having such properties as to absorb the laser beams generated in said laser generating device.

2. The methane/methanol producing system as claimed in claim 1 further comprising a wavelength adjusting member provided in a laser beam transmission path for converting or shifting the wavelength of the laser beams.

3. The methane/methanol producing system as claimed in claim 2 wherein said laser generating device comprises a sunlight-excited solid laser which comprises a condensing lens for condensing sunlight at high density and one or a plurality of said laser rods arranged in parallel at predetermined spacings, optical resonators comprising reflecting mirrors provided at both ends of said each laser rod, and a light reflecting member surrounding said laser rods, sunlight condensed by said condensing lens being irradiated on said each laser rod or passed a plurality of times through said each laser rod by reflecting by said reflecting mirror, thereby generating radial light in said laser rods by the action of said laser activating substance by amplifying and oscillating the radiant light by means of said optical resonators.

4. The methane/methanol producing system as claimed claim 2 wherein said each laser rod is formed of a laser medium having the maximum absorbing property within the peak wavelength of the optical energy density of sunlight or within a predetermined range.

5. The methane/methanol producing system as claimed in claim 1 wherein said laser generating device comprises a sunlight-excited solid laser which comprises a condensing lens for condensing sunlight at high density and one or a plurality of said laser rods arranged in parallel at predetermined spacings, optical resonators comprising reflecting mirrors provided at both ends of said each laser rod, and a light reflecting member surrounding said laser rods, sunlight condensed by said condensing lens being irradiated on said each laser rod or passed a plurality of times through said each laser rod by reflecting by said reflecting mirror, thereby generating radial light in said laser rods by the action of said laser activating substance by amplifying and oscillating the radiant light by means of said optical resonators.

6. The methane/methanol producing system as claimed in claim 5 wherein said light reflecting member comprises a clad portion that is different in reflectance from said laser rods, said laser rods being buried in said clad portion.

7. The methane/methanol producing system as claimed claim 6 wherein an aspect ratio which is a ratio of the diameter to length of said laser rods is equal to or greater than a predetermined value to suppress the diverging angle of laser beams to transmit them such that diversion of the laser beams transmitted to a light-receiving facility on the earth will be less than 100 meters.

8. The methane/methanol producing system as claimed in claim 5 wherein said light reflecting member comprises a reflective surface having a coating of a high reflectance and provided on the inner surface of a hollow cavity.

9. The methane/methanol producing system as claimed in claim 8 wherein a clad layer is provided on the outer periphery of said each laser rod in said hollow cavity to adjust the refractive index of said laser rod.

10. The methane/methanol producing system as claimed claim 9 wherein an aspect ratio which is a ratio of the diameter to length of said laser rods is equal to or greater than a predetermined value to suppress the diverging angle of laser beams to transmit them such that diversion of the laser beams transmitted to a light-receiving facility on the earth will be less than 100 meters.

11. The methane/methanol producing system as claimed claim 8 wherein an aspect ratio which is a ratio of the diameter to length of said laser rods is equal to or greater than a predetermined value to suppress the diverging angle of laser beams to transmit them such that diversion of the laser beams transmitted to a light-receiving facility on the earth will be less than 100 meters.

12. The methane/methanol producing system as claimed claim 5 wherein an aspect ratio which is a ratio of the diameter to length of said laser rods is equal to or greater than a predetermined value to suppress the diverging angle of laser beams to transmit them such that diversion of the laser beams transmitted to a light-receiving facility on the earth will be less than 100 meters.

13. The methane/methanol producing system as claimed claim 5 wherein said each laser rod is formed of a laser medium having the maximum absorbing property within the peak wavelength of the optical energy density of sunlight or within a predetermined range.

14. The methane/methanol producing system as claimed claim 1 wherein said each laser rod is formed of a laser medium having the maximum absorbing property within the peak wavelength of the optical energy density of sunlight or within a predetermined range.

15. The methane/methanol producing system as claimed in claim 14 wherein said laser medium comprises at least one kind of laser activating substance having the maximum absorbing properties within the peak wavelength of the optical energy density of sunlight or within a predetermined range.

* * * * *